(12) United States Patent
Leung et al.

(10) Patent No.: US 7,371,253 B2
(45) Date of Patent: May 13, 2008

(54) SUTURE ANCHOR AND METHOD

(75) Inventors: Jeffrey C. Leung, Raleigh, NC (US); Gregory Ruff, Chapel Hill, NC (US); Andrew Kaplan, Hillsborough, NC (US)

(73) Assignee: Quill Medical, Inc., North Bend, WA (US)

( * ) Notice: Subject to any disclaimer, the term of this patent is extended or adjusted under 35 U.S.C. 154(b) by 449 days.

(21) Appl. No.: 10/914,755

(22) Filed: Aug. 9, 2004

(65) Prior Publication Data

US 2005/0033367 A1 Feb. 10, 2005

Related U.S. Application Data

(62) Division of application No. 10/216,516, filed on Aug. 9, 2002, now Pat. No. 6,773,450.

(51) Int. Cl.
*A61B 17/04* (2006.01)
(52) U.S. Cl. .................................... 606/228
(58) Field of Classification Search ............... 606/72, 606/228–232; 128/898
See application file for complete search history.

(56) References Cited

U.S. PATENT DOCUMENTS

| | | |
|---|---|---|
| 879,758 A | 2/1908 | Foster |
| 1,248,825 A | 12/1917 | Dederer |

(Continued)

FOREIGN PATENT DOCUMENTS

EP 0 428 253 B1 7/1994

(Continued)

OTHER PUBLICATIONS

Hongtao Han, et al.; Mating and Piercing Micromechanical Structures for Surface Bonding Applications; 1991; pp. 253-258.

(Continued)

*Primary Examiner*—Julian W. Woo
(74) *Attorney, Agent, or Firm*—Moore & Van Allen, PLLC; Michael G. Johnston; Jennifer L. Skord

(57) ABSTRACT

A suture anchor for approximating tissue to bone comprises an anchor member for securing the suture anchor to the bone and a plurality of sutures mounted to the anchor member so that the sutures extend outwardly from the anchor member. Each suture has a sharp pointed end for penetrating the tissue and a plurality of barbs which permit movement of the sutures through the tissue in one direction of movement of the pointed end and prevent movement of the sutures relative to the tissue in the opposite direction. The ends of the sutures are inserted and pushed through the tissue along a curvilinear path in a direction away from the bone. The sutures are drawn from exit points longitudinally spaced from the points of insertion and reinserted and advanced along a curvilinear path in the direction away from the bone. The sutures are drawn through the tissue while approximating the tissue adjacent the bone along the suture and leaving a length of the sutures in the tissue. The exit and entry points of two of the sutures are adjacent and the paths of the sutures substantially mirror one another.

25 Claims, 11 Drawing Sheets

U.S. PATENT DOCUMENTS

| | | | |
|---|---|---|---|
| 2,355,907 A | 8/1944 | Cox | |
| 2,572,936 A | 10/1951 | Kulp et al. | |
| 2,866,256 A | 12/1958 | Matlin | |
| 3,003,155 A | 10/1961 | Mielzynski et al. | |
| 3,646,615 A | 3/1972 | Ness | |
| 3,833,972 A | 9/1974 | Brumlik | |
| 3,918,455 A | 11/1975 | Coplan | |
| 3,981,307 A | 9/1976 | Borysko | |
| 4,069,825 A | 1/1978 | Akiyama | |
| 4,198,734 A | 4/1980 | Brumlik | |
| 4,316,469 A | 2/1982 | Kapitanov | |
| 4,493,323 A | 1/1985 | Albright et al. | |
| 5,084,063 A | 1/1992 | Korthoff | |
| 5,102,418 A | 4/1992 | Granger et al. | |
| 5,112,344 A | 5/1992 | Petros | |
| 5,123,911 A | 6/1992 | Granger et al. | |
| 5,123,919 A | 6/1992 | Sauter et al. | |
| 5,217,494 A | 6/1993 | Coggins et al. | |
| 5,258,013 A | 11/1993 | Granger et al. | |
| 5,269,783 A * | 12/1993 | Sander | 606/72 |
| 5,292,326 A | 3/1994 | Green et al. | |
| 5,374,268 A | 12/1994 | Sander | |
| 5,500,991 A | 3/1996 | Demarest et al. | |
| 5,533,982 A | 7/1996 | Rizk et al. | |
| 5,683,417 A | 11/1997 | Cooper | |
| 5,716,376 A | 2/1998 | Roby et al. | |
| 5,722,991 A | 3/1998 | Colligan | |
| 5,887,594 A | 3/1999 | LoCicero, III | |
| 5,931,855 A * | 8/1999 | Buncke | 606/228 |
| 5,984,933 A | 11/1999 | Yoon | |
| 6,083,244 A | 7/2000 | Lubbers et al. | |
| 6,102,947 A * | 8/2000 | Gordon | 606/228 |
| 6,163,948 A | 12/2000 | Esteves et al. | |
| 6,241,747 B1 | 6/2001 | Ruff | |
| 6,270,517 B1 | 8/2001 | Brotz | |
| 6,443,962 B1 | 9/2002 | Gaber | |
| 6,478,809 B1 | 11/2002 | Brotz | |
| 6,599,310 B2 | 7/2003 | Leung et al. | |
| 6,645,226 B1 | 11/2003 | Jacobs et al. | |
| 2003/0149447 A1 | 8/2003 | Morency et al. | |
| 2004/0030354 A1 | 2/2004 | Leung et al. | |

FOREIGN PATENT DOCUMENTS

| | | |
|---|---|---|
| EP | 0 576 337 B1 | 5/1997 |
| FR | 2 619 129 | 2/1989 |
| JP | 1 506 362 | 4/1978 |
| WO | WO 99/21488 | 5/1999 |

OTHER PUBLICATIONS

H.J. Buncke, et al.; The Suture Repair of One-Millimeter Vessels; Micro-Vascular Surgery; Oct. 6-7, 1966; pp. 24-35.

M.A. Sulamanidze, et al.; Removal of Facial Soft Tissue Ptosis with Special Threads; Dermatol Surg 2002; vol. 28; pp. 367-371.

* cited by examiner

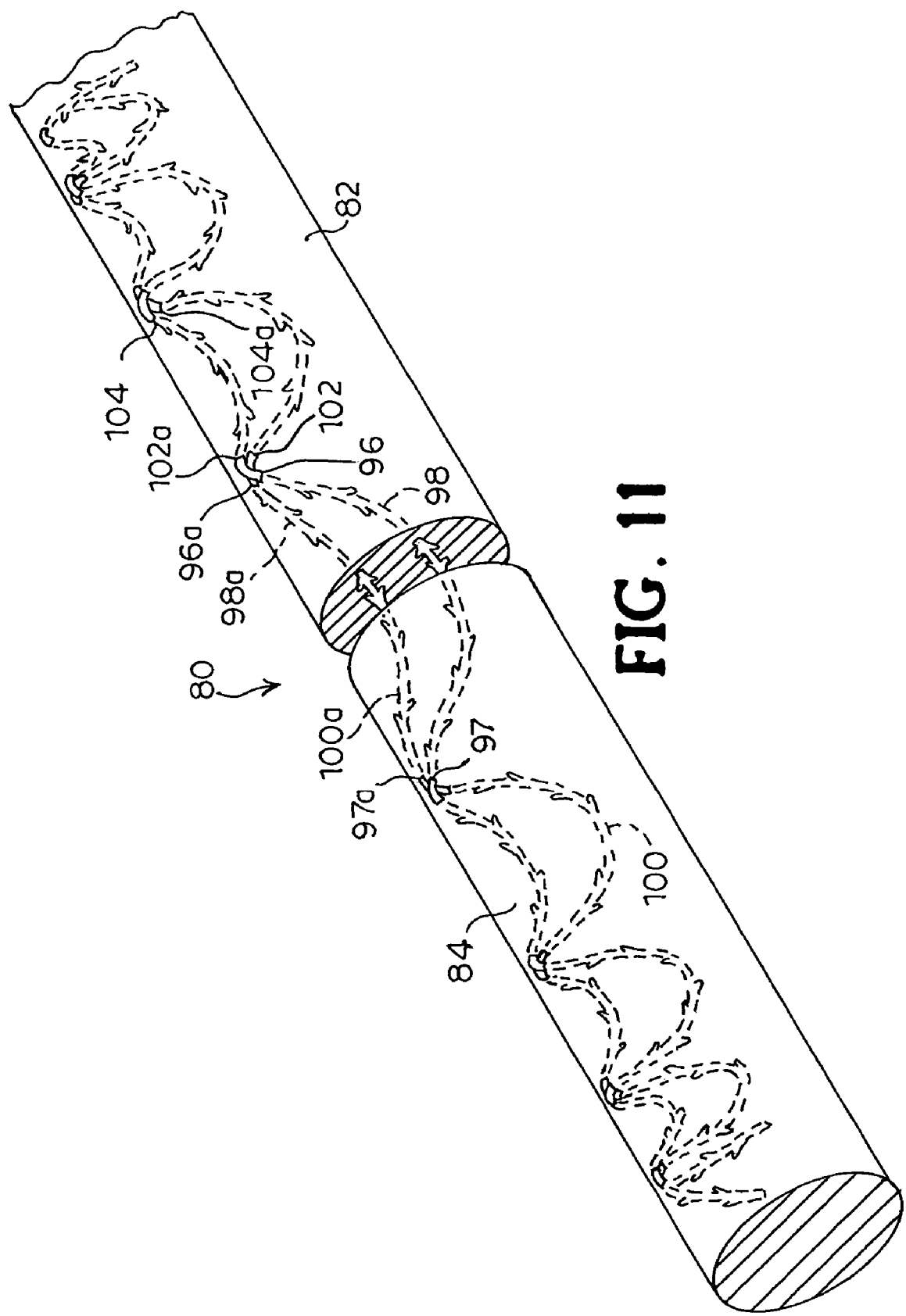

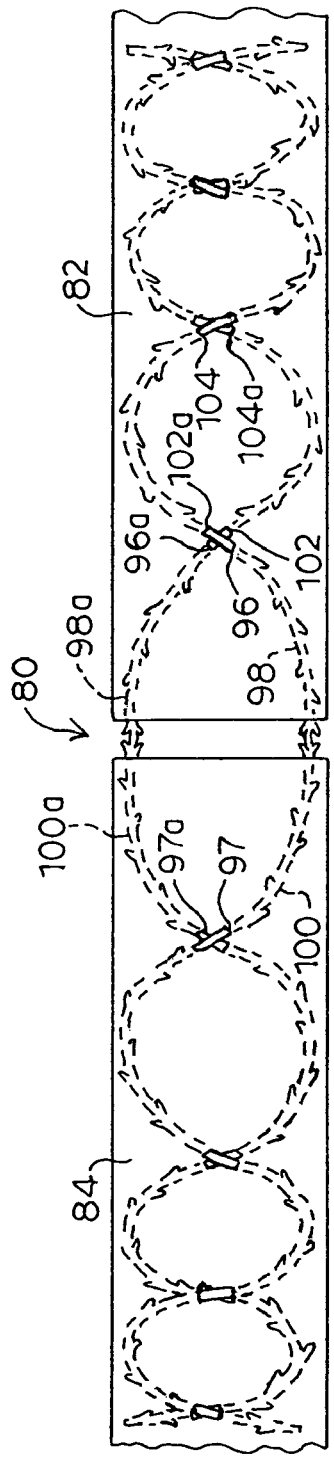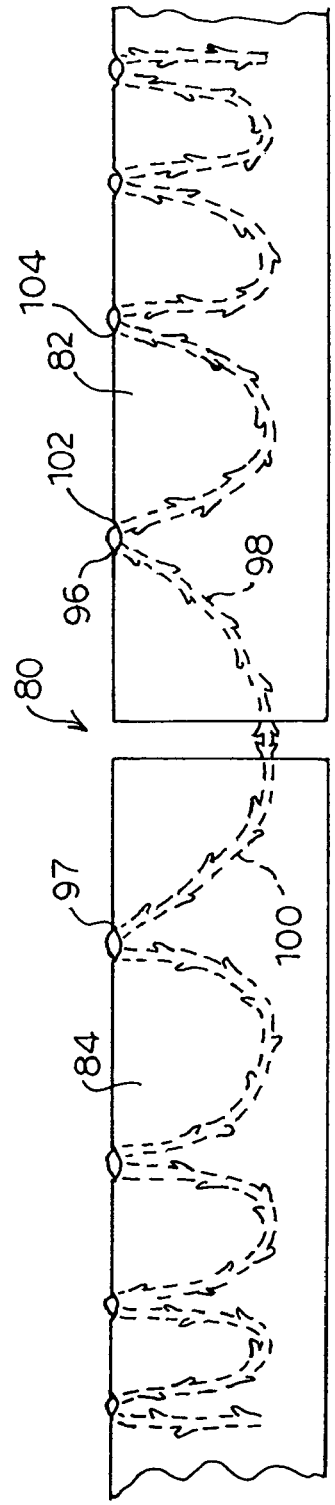

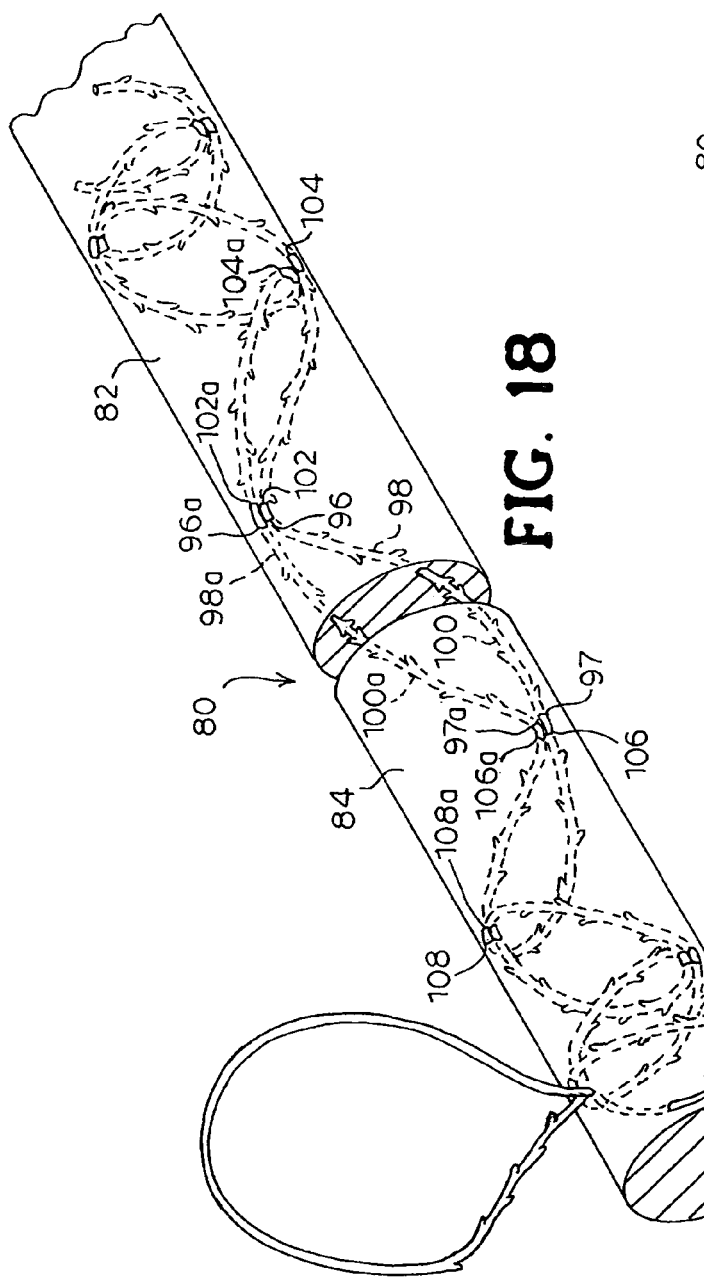
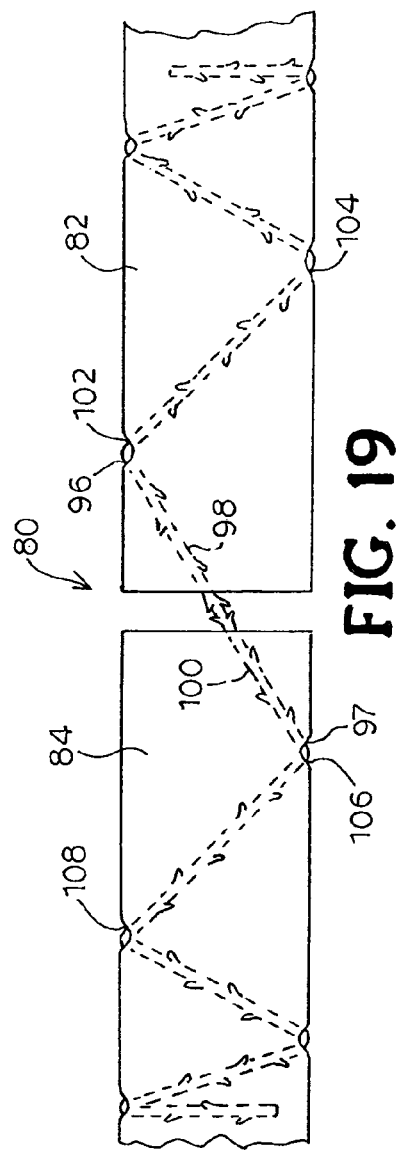

SUTURE ANCHOR AND METHOD

This application is a divisional application of application Ser. No. 10/216,516, filed Aug. 9, 2002, and issued on Aug. 10, 2004 as U.S. Pat. No. 6,773,450, the contents of which are incorporated here by reference.

BACKGROUND

This invention relates generally to a device and method for anchoring tissue within a body and, more particularly, to a suture anchor for use in surgical procedures requiring attachment of tissue, such as ligaments, tendons and the like, to other, preferably harder or more fibrous, tissue, such as a bone surface.

Suture anchors are used in surgical procedures wherein it is necessary for a surgeon to attach tissue to the surface of bone, for example, during joint reconstruction and ligament repair or replacement. Suture anchors generally comprise an anchor portion for fixed attachment to the bone, and a suture portion extending from the anchor portion used to connect the tissue to the bone. The anchor portion is often a generally cylindrical body having a sharp pointed end. An impact tool is typically used for driving the pointed end of the anchor into the bone. The outer surface of the anchor portion may be barbed or serrated to prevent the suture anchor from being withdrawn from the bone. The outer surface of the anchor portion could also be threaded and a driver, turned by a conventional drill, used to seat the threaded anchor portion into the bone. The anchor portion may also be fitted into a hole formed in the bone.

With the anchor portion securely in the bone, the suture portion is used for securing the tissue to the bone. The procedure typically involves passing a needle with the suture attached through the tissue. The tissue is advanced along the suture and tension is applied to the suture to draw the tissue tightly against the bone. The needle is removed and the tissue is secured against the bone by knotting the ends of the suture extending from the tissue. The knot is brought down to the surface of the tissue and tightened sufficiently to secure the tissue and bone in close approximation to promote reattachment and healing. A sliding retainer is sometimes used with the suture to pin the tissue against the bone.

There are other conventional suture anchors for attaching tissue to bone. For example, the anchor portion could take other forms including a staple which is driven into the bone surface with the suture positioned between the staple legs and the staple web fixing the suture to the bone surface. Also, a pair of closely-spaced holes can be drilled in the bone for passing the suture into one hole and out the other. However, these procedures are often difficult to perform, particularly in areas with limited access, such as deep wounds.

Further, conventional methods for approximating tissue to bone using a suture are difficult and inefficient because the procedure requires manipulation of the suture for securing the tissue in place. This is a time-consuming part of most surgical procedures, particularly in microsurgery and endoscopic surgery where there is insufficient space to properly manipulate the suture.

For the foregoing reasons, there is a need for an improved suture anchor for use in surgical procedures. The new suture anchor should eliminate the need for tying the suture to hold the tissue against the bone or other tissue surface. The method for using the suture anchor in surgical applications should allow a surgeon to approximate tissue to the bone or tissue surface in an efficient manner. A particularly useful new suture anchor would be used in surgical applications where space is limited such as microsurgery, endoscopic surgery or arthroscopic surgery.

SUMMARY

According to the present invention, a suture anchor is provided for approximating tissue to bone or other tissue. The suture comprises an anchor member adapted to fixedly engage the bone for securing the anchor member relative to the bone. A plurality of sutures are mounted to the proximal end of the anchor member so that the sutures extend outwardly from the anchor member. Each suture has a sharp pointed distal end for penetrating the tissue and a plurality of barbs extending from the periphery of the body. The barbs permit movement of the sutures through the tissue in a direction of movement of the pointed end and prevent movement of the sutures relative to the tissue in a direction opposite the direction of movement of the pointed end.

Also according to the present invention, a method is provided for approximating tissue to a bone or other tissue to allow reapproximation and healing of the tissue and bone in vivo. The method uses a suture anchor including an anchor member adapted to be fixedly mounted to the bone and a plurality of sutures extending from the anchor member. The method comprises the steps of providing on each suture a sharp pointed distal end for penetrating the tissue and a plurality of barbs extending from the periphery of the body. The barbs permit movement of the sutures through the tissue in a direction of movement of the pointed end and prevent movement of the sutures relative to the tissue in a direction opposite the direction of movement of the pointed end. The anchor member is secured in the bone such that the sutures extend from the bone surface and a pointed end of a first suture is inserted into the tissue. The end of the first suture is pushed through the tissue along a curvilinear path in a direction away from the bone until the point at the end of the first suture extends out of the tissue at an exit point in the periphery of the tissue longitudinally spaced from the point of insertion. The pointed end of the first suture is gripped and pulled out of the tissue for drawing the first suture through the tissue while approximating the tissue adjacent the bone along the suture and leaving a length of the first suture in the tissue. The pointed end of the first suture is then inserted into the periphery of the tissue adjacent the exit point and pushed through the tissue along a curvilinear path in the direction away from the bone until the pointed end of the first suture extends out of the tissue at an exit point in the periphery of the tissue longitudinally spaced from the previous insertion point. The pointed end of the first suture is gripped and pulled out of the tissue for drawing the first suture through the tissue leaving a length of the first portion of the suture in the tissue. These steps are repeated with the first suture for advancing longitudinally along the tissue in the direction away from the bone. A second suture is then introduced into the tissue and the previous steps repeated so that the exit and entry points of the second suture are adjacent the corresponding exit and entry points of the first suture and the path of the second suture substantially mirrors the path of the first suture.

BRIEF DESCRIPTION OF DRAWINGS

For a more complete understanding of the present invention, reference should now be had to the embodiments shown in the accompanying drawings and described below. In the drawings:

FIGS. 11-13 are perspective, side and top plan views, respectively, of the suture pattern generated by the method shown in FIGS. 7-10;

FIGS. 18 and 19 are perspective and side elevation views, respectively, of the suture pattern generated by the method shown in FIGS. 14-17.

DESCRIPTION

As used herein, the term "tissue" includes tendons, ligaments, cartilage, muscle, skin, organs, and other soft tissue. The term "bone" includes bone, cartilage, tendon, ligament, fascia, and other connective or fibrous tissue suitable for anchor for a suture.

Certain other terminology is used herein for convenience only and is not to be taken as a limitation on the invention. For example, words such as "upper," "lower," "left," "right," "horizontal," "vertical," "upward," and "downward" merely describe the configuration shown in the FIGS. It is understood that the components may be oriented in any direction and the terminology, therefore, should be understood as encompassing such variations unless specified otherwise.

Figure 1:
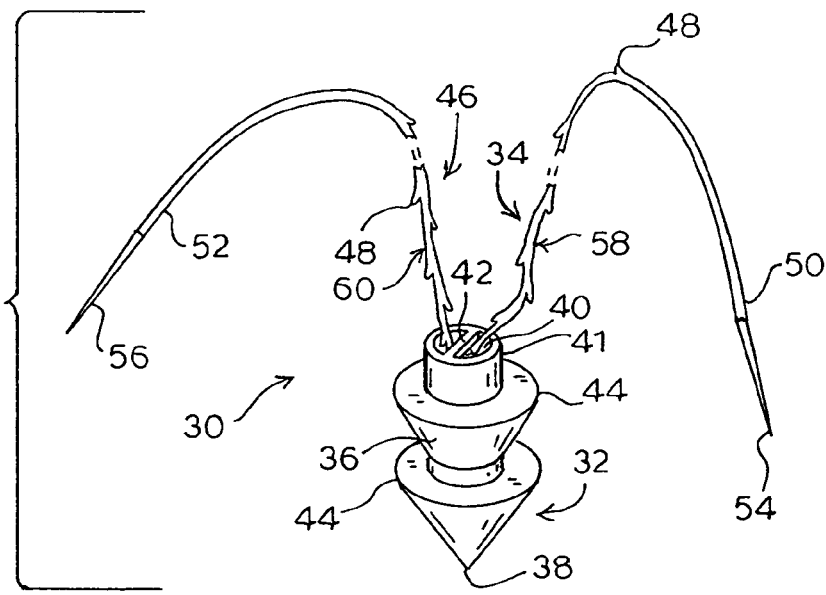
FIG. 1 is a perspective view of an embodiment of a suture anchor according to the present invention.

Referring now to the drawings, wherein like reference numerals designate corresponding or similar elements throughout the several views, there is shown in FIG. 1 a suture anchor for use according to the present invention and generally designated at 30. The suture anchor 30 includes an anchor portion 32 and a suture portion 34. The anchor portion 32 comprises an elongated body 36 having a distal pointed tip 38 which serves as a leading end of the suture anchor 30 when the suture anchor is inserted into bone. A blind bore 40, or opening, is formed at the proximal end 41 of the anchor portion 32. A crossbar 42 integral with the anchor body 36 spans the opening 40 for threadably receiving the suture portion 34 at the proximal end of the anchor portion 32.

The anchor portion 32 is shown as having a circular cross-section, although other cross-sectional shapes could be utilized without departing from the present invention. As shown in FIG. 1, ridges 44, or barbs, may be formed on the outer surface of the anchor portion 32 which allow movement of the anchor portion 32 through bone in one direction but which resist the withdrawal of the anchor portion 32 after the anchor portion has been implanted in the bone.

As described above, the anchor portion 32 is driven into the bone surface, pointed tip 38 first, by impact against the proximal end 41, or by turning as when the anchor portion 32 is threaded (not shown). The anchor portion 32 can also be disposed into a hole bored in the bone, in which case insertion can be accomplished with direct pressure or gentle tapping on the proximal end 41 of the anchor portion 32. The ridges 44 on the surface of the anchor body 36 grasp the bone rendering the anchor portion 32 substantially irremovable from the bone. Tension on the suture portion 34 enhances this effect.

The suture portion 34 of the suture anchor 30 has an elongated body 46 and a plurality of barbs 48 disposed along the length of the body 46. First and second ends 50, 52 of the suture body 46 terminate in points 54, 56 for penetrating tissue. The body 46 of the suture portion 34 is, in one embodiment, circular in cross section. Suitable diameters for the body 46 range from about 0.001 mm to about 5.0 mm. The body 46 of the suture portion 34 could also have a non-circular cross-sectional shape which would increase the surface area of the body 46 and facilitate the formation of multiple barbs 48. The length of the suture portion 34 can vary depending on several factors, including the desired surgical application, the type of tissue to be approximated to the bone, the location of the bone, and the like. A suture portion 34 of proper length is selected for achieving suitable results in a particular application.

The plurality of barbs 48 is axially-spaced along the body 46 of the suture portion 34. The barbs 48 are oriented in one direction facing toward the first end 50 of the suture body 46 for a first portion 58 of the length of the suture portion 34 and in an opposite direction facing the second end 52 of the suture body 46 for a second portion 60 of the suture portion 34. The point on the suture body 46 where the barbs 48 change direction is preferably positioned adjacent the crossbar 42 at the proximal end of the anchor body 36. The barbs 48 are yieldable toward the body 46. The barbs 48 on each portion 58, 60 of the suture body 46 are oriented so as to allow movement of the suture portion 34 through the tissue in one direction along with the corresponding end 50, 52 of the suture portion 34. The barbs 48 are generally rigid in an opposite direction to prevent the suture body 46 from moving in the tissue in the opposite direction.

The barbs 48 can be arranged in any suitable pattern, for example, in a helical pattern as shown in FIG. 1. The number, configuration, spacing and surface area of the barbs 48 can vary depending upon the tissue in which the suture portion 34 is used, and depending on the composition and geometry of the suture body 46. The proportions of the barbs 48 may remain relatively constant while the overall length and spacing of the barbs 48 are determined by the tissue being approximated to the bone. For example, if the suture portion 34 is intended to be used in tendon, the barbs 48 can be made relatively short and more rigid to facilitate entry into this rather firm, fibrous tissue. If the suture portion 34 is intended for use in soft tissue, such as fat, the barbs 48 can be made longer and spaced farther apart to increase the holding ability in the soft tissue. Moreover, the ratio of the number of barbs 48 on the first portion 58 of the suture body 46 to the number of barbs 48 on the second portion 60, and the lengths of each portion 58, 60, can vary depending on the surgical application and needs.

The surface area of the barbs 48 can also vary. For example, fuller-tipped barbs 48 can be made of varying sizes designed for specific surgical applications. For joining fat and relatively soft tissues, larger barbs 48 are desired, whereas smaller barbs 48 are more suited for collagen-dense tissues. There are also situations where a combination of large and small barbs 48 within the same structure will be beneficial such as when the suture portion 34 is used in the repair of tissue with differing layered structures. Use of the combination of large and small barbs 48 with the same suture portion 34 wherein barb 48 sizes are customized for each tissue layer will ensure maximum anchoring properties.

The barbs 48 may be formed on the surface of the suture body 46 according to any suitable method, including cutting, molding, and the like. The preferred method is cutting with acute angular cuts directly into the suture body 46 with the cut portions pushed outwardly and separated from the body 46. The depth of the barbs 48 formed in the suture body 46 depends on the diameter of the suture material and the depth of cut. Embodiments of a suitable cutting device for cutting a plurality of axially spaced barbs 48 on the exterior of suture filaments are shown and described in U.S. patent application Ser. No. 09/943,733, entitled "Method Of Forming Barbs On A Suture And Apparatus For Performing Same", which was filed on Aug. 31, 2001, the contents of which are hereby incorporated by reference. This cutting device utilizes a cutting bed, a cutting bed vise, a cutting template, and a blade assembly to perform the cutting. When operated, the cutting device has the ability to produce a plurality of axially spaced barbs 48 in the same or random configuration and at different angles in relation to each other. Various other suitable methods of cutting the barbs 48 have been proposed including the use of a laser. The barbs 48 could also be cut manually. However, manually cutting the barbs 48 is labor intensive, decreases consistency, and is not cost effective. The suture portion 34 could also be formed by injection molding, extrusion, stamping and the like.

Barbed sutures suitable for use according to the methods of the present invention are described in U.S. Pat. No. 5,342,376, entitled "Inserting Device for a Barbed Tissue Connector", U.S. Pat. No. 6,241,747, entitled "Barbed Bodily Tissue Connector", and U.S. Pat. No. 5,931,855. The contents of U.S. Pat. No. 5,342,376, U.S. Pat. No. 5,931,855 and U.S. Pat. No. 6,241,747 are hereby incorporated by reference.

The suture portion 34 is attached to the proximal end of the anchor portion 32. As seen in FIG. 1, the suture portion 34 is threaded around the crossbar 42 on the anchor body 36. It is understood that the suture portion 34 may be attached to the anchor portion 32 in a number of ways, including inserting the end of the suture body 46 into the bore 40 formed in the proximal end of the anchor body 36 and securing the suture body 46 in place with a set screw, rivet, or the like, or, wherein the material of the anchor portion 32 is metal, by swaging or crimping. The anchor portion 32 and suture portion 34 could also be formed in one piece in the manufacturing process. However, the preferred attachment of the suture portion 34 is as shown in FIG. 1 since this arrangement allows a simple, secure threading of a double-ended suture portion 34 during manufacture or prior to use. Moreover, as seen in FIG. 2, the user may selectively attach several suture portions 34 to the anchor portion 32 depending upon the surgical application.

Suitable material for the body 46 of the suture portion 34 is available in a wide variety of monofilament suture material. The particular suture material chosen depends on strength and flexibility requirements. In one embodiment, the material for the suture body 46 is flexible and substantially nonresilient so that the shape of an inserted suture portion 34 will be determined by the path of insertion and the surrounding tissue. In some applications, however, it may be desirable for at least a portion of the suture body 46 to have sufficient dimensional stability to assume a substantially rigid configuration during use and sufficient resiliency to return to a predetermined position after deflection therefrom. The portions of the ends 50, 52 of the suture body 46 adjacent the points 54, 56 may be formed of a material sufficiently stiff to enable the points 54, 56 to penetrate tissue in which the suture portion 34 is used when a substantially axial force is applied to the body 46. Variations in surface texture of the suture body 46 can impart different interaction characteristics with the tissue.

Figure 2:
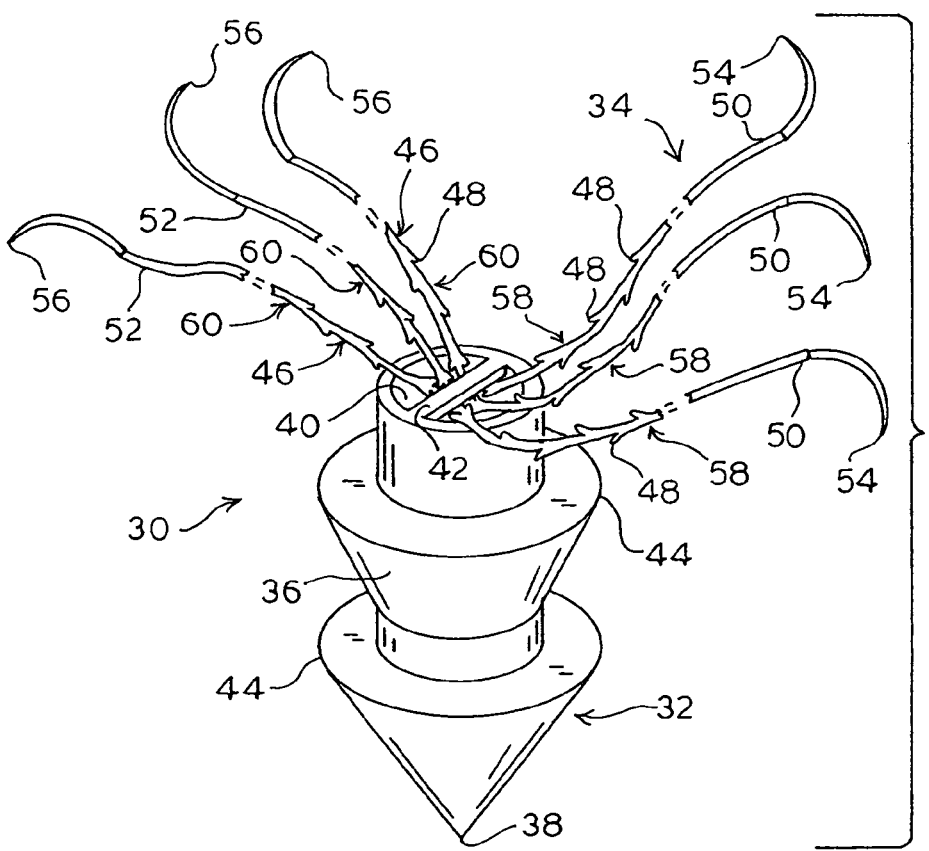
FIG. 2 is a perspective view of another embodiment of a suture anchor including a plurality of barbed sutures according to the present invention.

The ends 50, 52 of the suture portion 34 may be straight (FIG. 1) or curved (FIG. 2). In one embodiment, the ends 50, 52 of the suture portion 34 may be surgical needles secured at each end of the suture portion 34 so that the body 46 extends between the shank ends of the two needles. The needles are preferably constructed of stainless steel or other surgical-grade metal alloy. The needles may be secured to the suture body 46 by means of adhesives, crimping, swaging, or the like, or the joint may be formed by heat shrinkable tubing. A detachable connection may also be employed such that the needles may be removed from the suture body 46 by a sharp tug or pull or by cutting. The length of the needles is selected to serve the type of tissue being repaired so that the needles can be completely removed leaving the suture body 46 in the desired position within the tissue.

The suture anchor 30 of the present invention can be formed of a bioabsorbable material which allows the suture anchor 30 to be absorbed by the body over time. Bioabsorbable material is particularly useful in arthroscopic surgery and procedures. Many compositions useful as bioabsorbable materials can be used to make the suture anchor 30. Generally, bioabsorbable materials are thermoplastic polymers. Selection of the particular material is determined by the desired absorption or degradation time period which depends upon the anticipated healing time for the subject of the procedure. Biodegradable polymers and co-polymers range in degradation time from about one month to over twenty-four months. They include, but are not limited to, polydioxanone, polylactide, polyglycolide, polycaprolactone, and copolymers thereof. Other copolymers with trimethylene carbonate can also be used. Examples are PDS II (polydioxanone), Maxon (copolymer of 67% glycolide and 33% trimethylene carbonate), and Monocryl (copolymer of 75% glycolide and 25% caprolactone). Germicides can also be incorporated into the suture anchor 30 to provide long lasting germicidal properties.

Alternatively, either the anchor portion 32 or the suture portion 34 of the suture anchor 30 can be formed from non-absorbable material such as, for example, nylon, polyethylene terephthalate (polyester), polypropylene, and expanded polytetrafluoroethylene (ePTFE). The suture body 46 can also be formed of metal (e.g. steel), metal alloys, or the like. Titanium is a preferred material when the anchor portion 32 is to remain permanently in the bone. A suitable anchor portion 32 for use according to the present invention is available from Mitek Products of Norwood, Mass. Alternatively, the anchor portion 32 can also be a rigid barbed structure made from thick monofilament suture material with barbs suitable for anchoring in bone.

In use in an orthopedic surgical procedure, the anchor portion 32 of the suture anchor 30 of the present invention is inserted into bone. Once the anchor portion 32 is fixed in place, the suture portion 34 extends outwardly from the anchor portion 32 and the bone for surgical suturing to tissue to be approximated to the bone. The tissue is brought into position over the suture anchor 30 site. The point 54 at one end 50 of the suture portion 34 is inserted into the tissue such that the point 54 pierces the tissue and the barbs 48 on the portion 58 of the suture body 46 corresponding to the one end 50 yield toward the body 46 to facilitate movement of the suture body as it is drawn through the tissue in the direction of insertion. The point 56 at the other end 52 of the suture portion 34 is also inserted into the tissue and advanced through the tissue in like manner. The tissue is then advanced along the suture portions 58, 60 within the tissue to close the gap between the tissue and the bone. The barbs 48 of the suture body 46 grasp the surrounding tissue and maintain the tissue in position adjacent to the bone during healing. The leading ends 50, 52 of the suture body 46 protruding from the tissue are then cut and discarded.

According to the present invention, a surgical procedure using the suture anchor 30 is provided for approximating a torn Achilles tendon to bone for reattachment and healing. It is understood that the applicants do not intend to limit the suture anchor 30 and method of the present invention to only the reattachment of the Achilles tendon.

Figure 4:
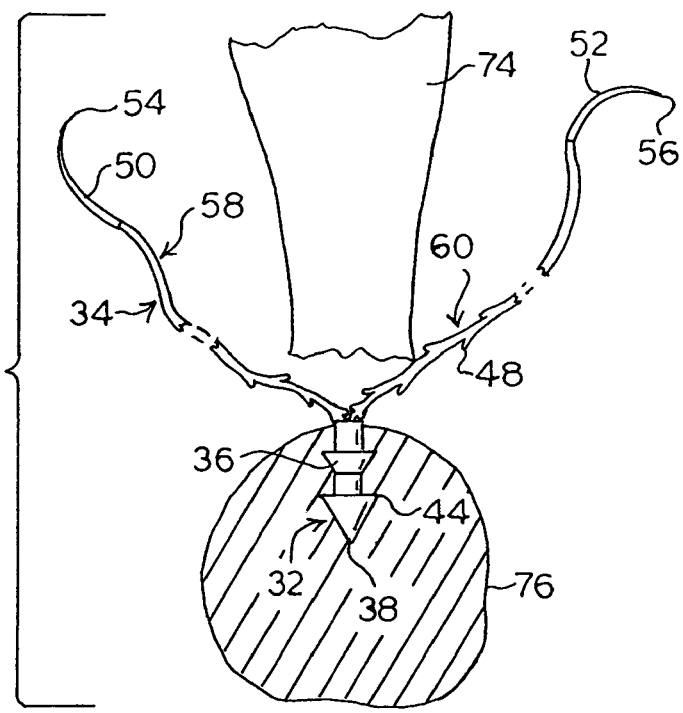
FIGS. 4-6 are schematic views of an embodiment of a method according to the present invention for reattaching the Achilles tendon to bone.
Figure 3:
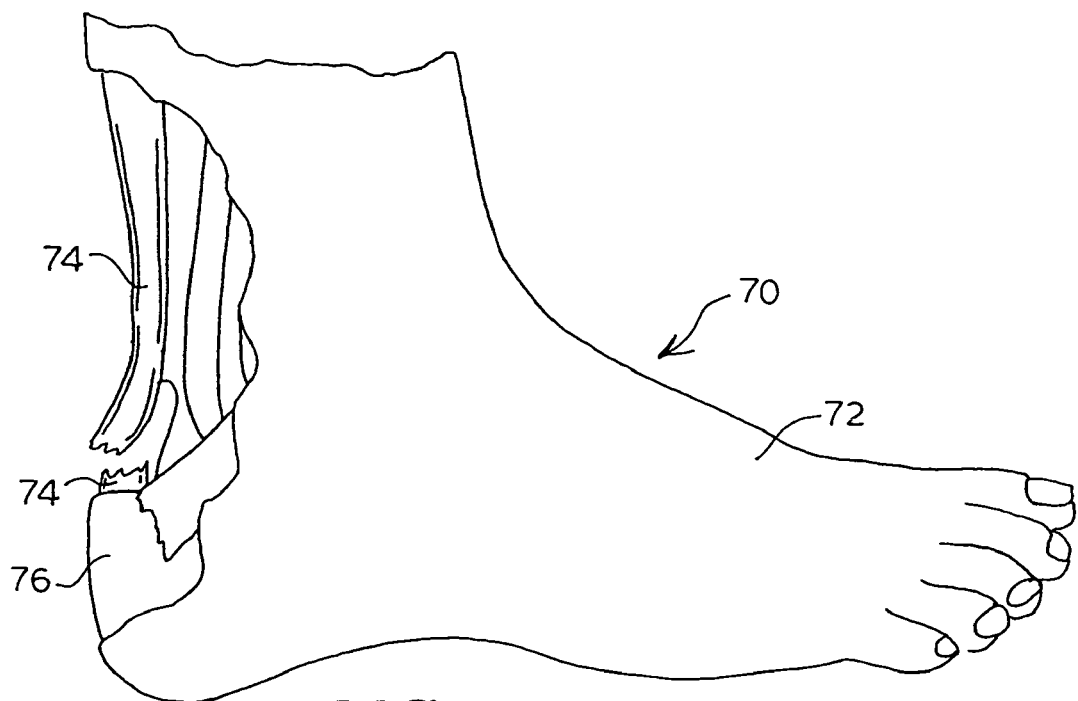
FIG. 3 is a side elevation view of an ankle with a portion of the outer layer of tissue cut-away to schematically show a torn Achilles tendon.

Referring to FIG. 3, a human foot 70 is shown with a portion of the outer layer 72 of skin and tissue cutaway to schematically show the Achilles tendon 74 torn away from the heel bone 76. In this embodiment of the present invention, the user, such as a surgeon, selects a suture anchor 30 (FIG. 4) having a suture portion 34 of sufficient length and having curved ends 50, 52 which, in one embodiment, as noted above may be surgical needles. As seen in FIG. 4, the surgeon begins by inserting the suture anchor 30 into the heel bone 76.

Figure 5:
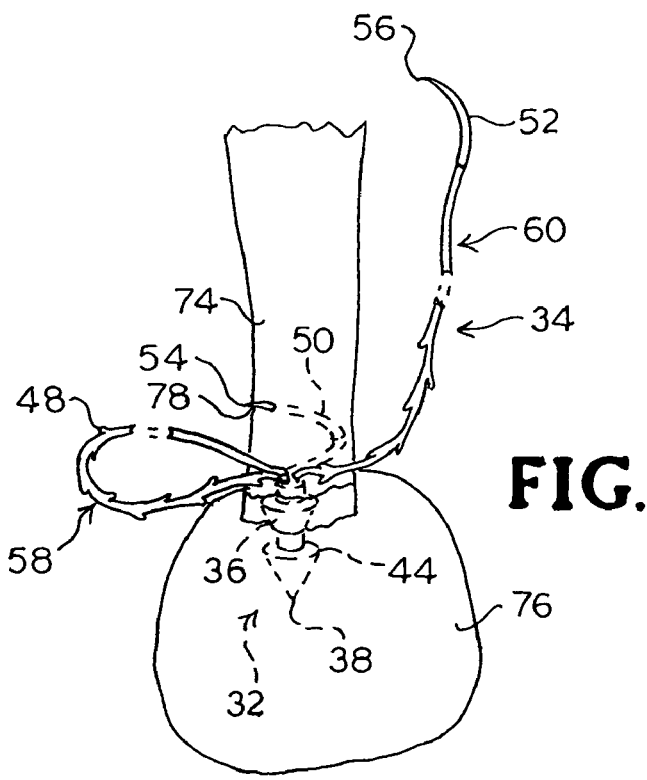
Figure 6:
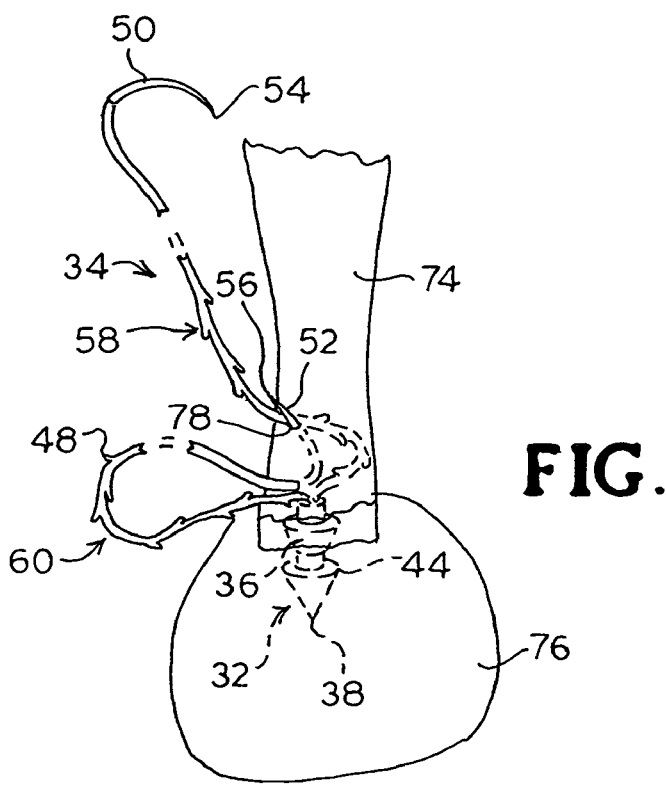

The first and second portions 58, 60 of the elongated suture portion 34 extend from the anchor portion 32. Next the surgeon inserts the first end 50 (FIG. 5), or surgical needle, into the free end of the Achilles tendon 74 and pushes the needle 50 through the tendon 74 along a selected curvilinear path until the point 54 at the first end of the needle 50 extends from an exit point 78 at the periphery of the tendon 74 longitudinally spaced from the end of the tendon. The surgeon grips the needle 50 and pulls the needle out of the tendon 74 for drawing the first portion 58 of the suture body 46 through the tendon 74 leaving a length of the first portion 58 of the suture body 46 in the tendon 74 between the end of the tendon and the exit point 78, as seen in FIG. 6. These steps are repeated with the second portion 60 of the suture body 46 beginning with insertion into the end of the tendon 74.

Figure 7:
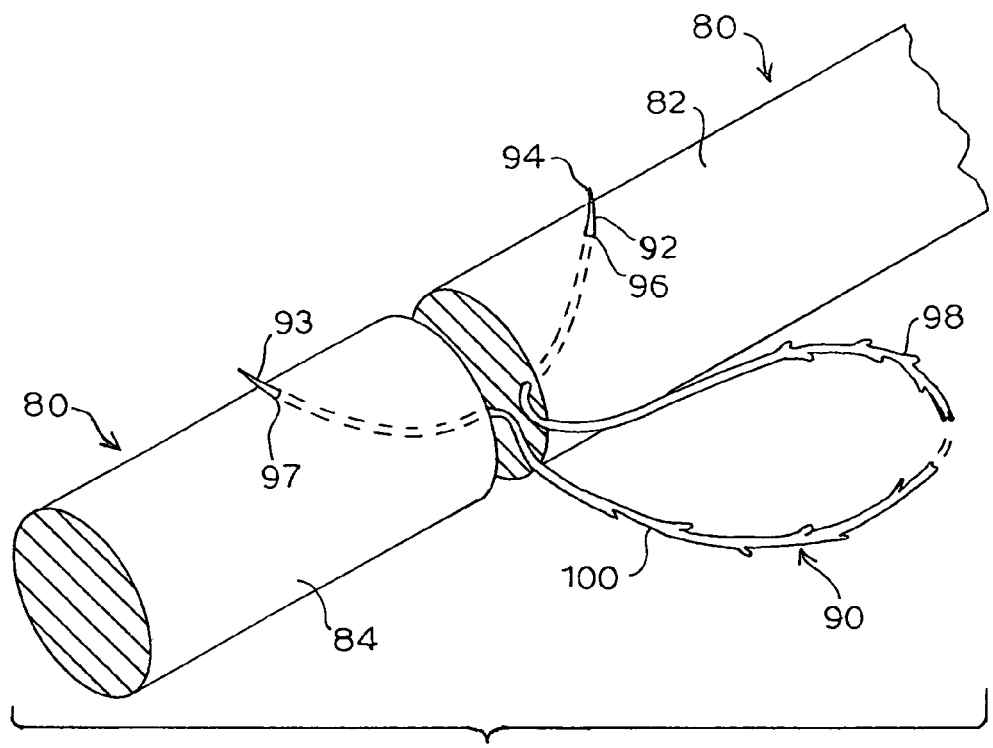
FIGS. 7-10 are perspective views of a method for joining two ends of a severed tendon according to the present invention.
Figure 8:
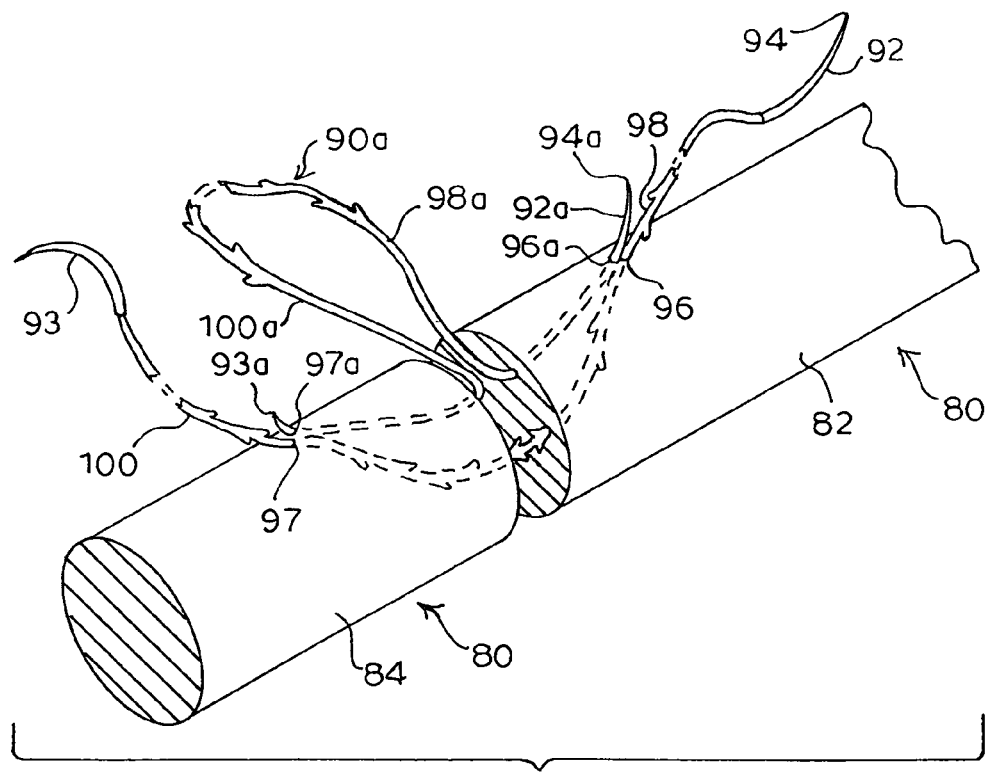

Methods according to the present invention useful in binding together partially or completely severed tendons, or other internal tissue repairs requiring considerable tensile strength, are suitable for use in attaching tissue to bone. One such method for joining two ends 82, 84 of a tendon 80 is shown in FIGS. 7-10. Referring to FIG. 7, the surgeon begins by inserting a first end 92 of a two-way barbed suture 90, which may comprise a straight or curved surgical needle, into one end 82 of the tendon 80 and pushing the needle 92 through the tendon 80 along a selected curvilinear path until the point 94 of the needle 92 extends from an exit point 96 in the periphery of the tendon 80 longitudinally spaced from the one end 82 of the tendon 80. The first needle 92 is gripped and pulled out of the tendon 80 for drawing a first portion 98 of the suture 90 through the tendon 80 leaving a length of the first portion 98 of the suture 90 in the tendon end 82 between the end of the tendon 80 and the exit point 96. As seen in FIG. 7, these steps are repeated with a second portion 100 of the suture 90 at the other end 84 of the tendon 80, wherein a second end 93 of the suture 90 is inserted into the tendon end 84 and advanced along a selected curvilinear path to an exit point 97 longitudinally spaced from the end 84 of the tendon 80. The second end 93 of the suture 90 projecting from the exit point 97 is gripped and pulled out of the tendon 80 for drawing the second portion 100 of the suture 90 through the tendon 80 and leaving a length of the second portion 100 of the suture 90 in the tendon end 84 (FIG. 8).

Referring now to FIG. 8, a second suture 90a is introduced into the ends 82, 84 of the tendon 80. The first needle 92a of the second suture 90a is inserted into the one end 82 of the tendon 80 and pushed through the tendon along a selected curvilinear path until the needle 92a extends from an exit point 96a in the periphery of the tendon 82 substantially co-located with the first exit point 96 of the first portion 98 of the first suture 90. These steps are repeated with the second portion 100a of the second suture 90a at the other end 84 of the tendon 80 such that the exit point 97a in the periphery of the end of the tendon 84 is substantially co-located with the first exit point 97 of the second portion 100 of the first suture 90. The needles 92a, 93a of the second suture 90a are pulled out of the tendon 80 for drawing the first and second portions 98a, 100a, respectively, of the second suture 90a through the tendon 80 leaving a length of the second suture 90a in the tendon 80 between the exit points 96a, 97a.

Figure 9:
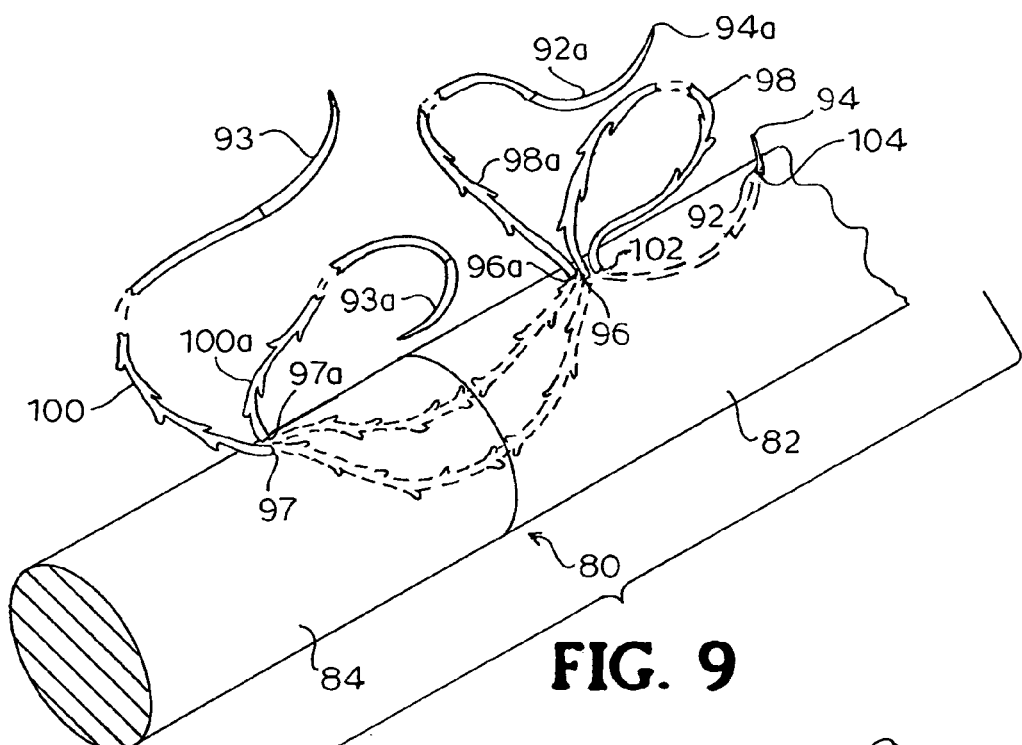
Figure 10:
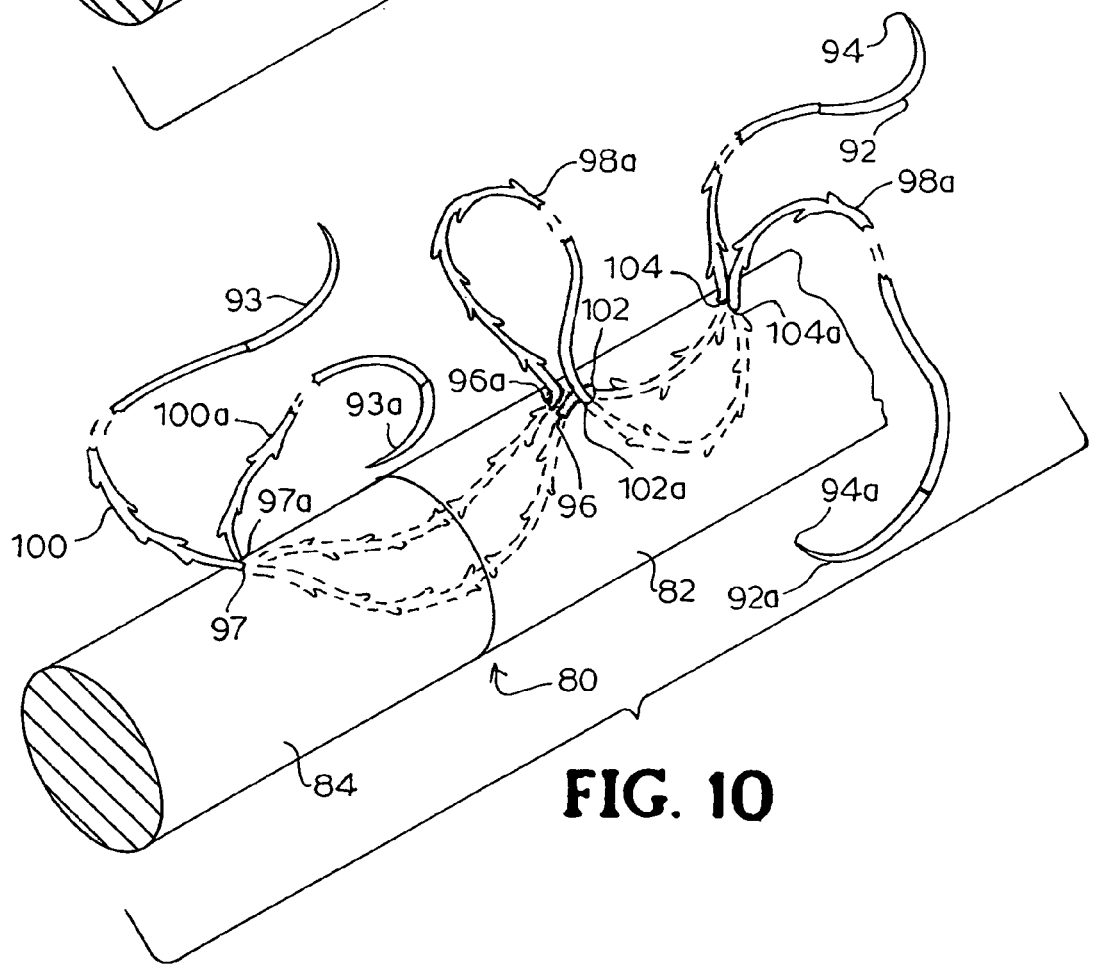

As shown in FIG. 9, the surgeon reinserts the first needle 92 of the first suture 90 into the periphery of the one end 82 of the tendon 80 at an entry point 102 immediately adjacent the exit point 96 and pushes the needle 92 along a selected curvilinear path until the point 94 of the needle 92 exits the same side of the tendon 82 at an exit point 104 that is longitudinally spaced from the entry point 102. It is understood that the surgeon could use the exit point 96 as the entry point 102 for the needle 92 if desired. The surgeon pulls the needle 92 out of the tendon 82 for drawing the first portion 98 of the suture 90 through the tendon 82. The surgeon may then reinsert the needle 92 into the tendon 82 at an entry point (not shown) immediately adjacent the exit point 104 and push the needle 92 along a selected curvilinear path and out of the same side of the tendon 82 at an exit point (not shown) longitudinally spaced from the previous entry point. It is understood that the surgeon makes as many passes as deemed necessary in a "wave-like" pattern for holding the end 82 of the tendon, or as the length or thickness of the tendon 82 allows, and removes the remaining length of the first portion 98 of the suture 90.

The surgeon repeats the steps described above with the first portion 98a of the second suture 90a (FIG. 10) by reinserting the needle 92a into the tendon 82 at an entry point 102a adjacent the exit point 96a, crossing over the first portion 98 of the first suture 90, and pushing the needle 92a along a selected curvilinear path until the needle 92a emerges from an exit point 104a in the periphery of the tendon 82 substantially co-located with the second exit point 104 of the first portion 98 of the first suture 90. In this manner, the surgeon advances longitudinally along the end 82 of the tendon 80 with the first portion 98a of the second suture 90a in a "wave-like" pattern which generally mirrors that of the first portion 98 of the first suture 90.

The previous steps are repeated at the other end 84 of the tendon 80 with the second portions 100, 100a of the first suture 90 and second suture 90a. The pattern of the second portions 100, 100a of the sutures 90, 90a in the second end 84 of the tendon 80 generally mirrors that of the first portions 98, 98a of the sutures in the first end 82 of the tendon 80. Thus, the exit points and entry points of the first and second sutures 90, 90a are substantially co-located.

The ends 82, 84 of the tendon 80 are brought together by pushing the tendon ends along the sutures while maintaining tension on the free ends 92, 92a, 93, 93a of the sutures 90, 90a. The barbs 48 maintain the sutures 90, 90a in place and resist movement of the tendon ends 82, 84 away from this position. The needles along with remaining lengths of the suture portions 98, 98a, 100, 100a are cut and discarded.

FIGS. 11-13 show the suture pattern resulting from use of the above-described method of the present invention. It is understood that we do not intend to limit ourselves to the depth or length of the suture paths shown in the FIGS. as the amount of tissue grasped by each pass, which is related to the depth of the suture path into the tissue and the length of the pass from entry point to exit point, may be determined by the surgeon based on a number of factors including the tissue to be joined.

Figure 14:
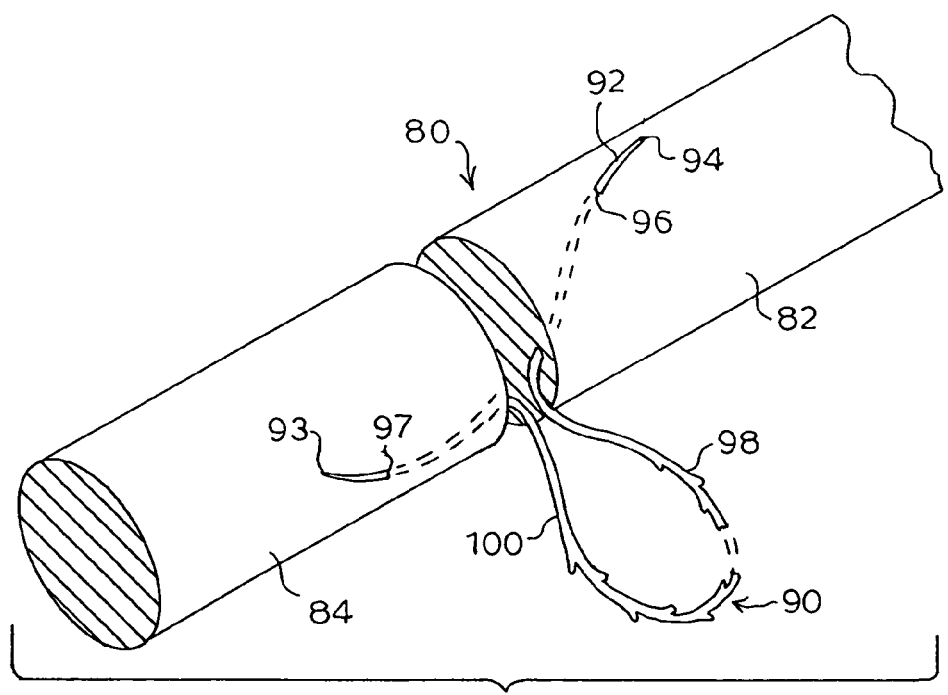
FIGS. 14-17 are perspective views of another method for joining two ends of a severed tendon according to the present invention.
Figure 15:
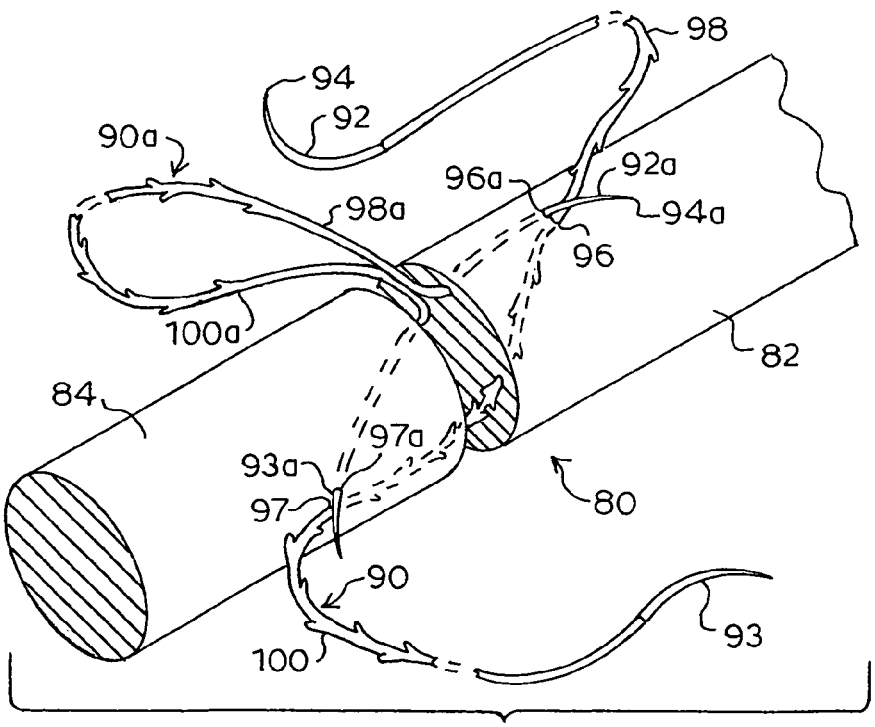

Another method according to the present invention for joining two ends 82, 84 of a tendon 80 which is suitable for use in attaching tissue to bone is shown in FIGS. 14-17. Referring to FIG. 14, the surgeon begins by inserting the first end 92 of a two-way barbed suture 90, which may comprise a straight or curved surgical needle, into one end 82 of the tendon 80 and pushing the needle 92 through the tendon 82 along a selected curvilinear path until the point 94 of the needle 92 extends from an exit point 96 in the periphery of the tendon 82 longitudinally spaced from the one end 82 of the tendon. The first needle 92 is gripped and pulled out of the tendon 82 for drawing the first portion 98 of the suture 90 through the tendon 80 leaving a length of the first portion 98 of the suture in the tendon 80 between the tendon end 82 and the exit point 96. As seen in FIG. 14, these steps are repeated with the second portion 100 of the suture 90 at the other end 84 of the tendon 80. That is, a second end 93 of the suture 90 is inserted into the tendon end 84 and advanced along a selected curvilinear path to an exit point 97 longitudinally spaced from the end 84 of the tendon 80. The exit point 97 of the second needle 93 is on the opposite side of the tendon 80 from the first exit point 96 of the first portion 98 of the suture 90. The second end 93 of the suture 90 projecting from the exit point 97 is gripped and pulled out of the tendon 80 for drawing the second portion 100 of the suture 90 through the tendon 80 and leaving a length of the second portion 100 of the suture 90 in the tendon end 84 (FIG. 15).

Referring now to FIG. 15, a second suture 90a is introduced into the ends 82, 84 of the tendon 80. The first needle 92a of the second suture 90a is inserted into the end 82 of the tendon 80 and pushed through the tendon along a selected curvilinear path until the needle 92a extends from an exit point 96a in the periphery of the tendon 82 substantially co-located with the first exit point 96 of the first portion 98 of the first suture 90. These steps are repeated with the second portion 100a of the second suture 90a at the other end 84 of the tendon 80 such that the exit point 97a in the periphery of the end of the tendon 84 is substantially co-located with the first exit point 97 of the second portion 100 of the first suture 90. The needles 92a, 93a of the second suture 90a are pulled out of the tendon 80 for drawing the first portion 98a and second portion 100a of the second suture 90a through the tendon 80 leaving a length of the second suture 90a in the tendon 80 between the exit points 96a, 97a.

Figure 16:
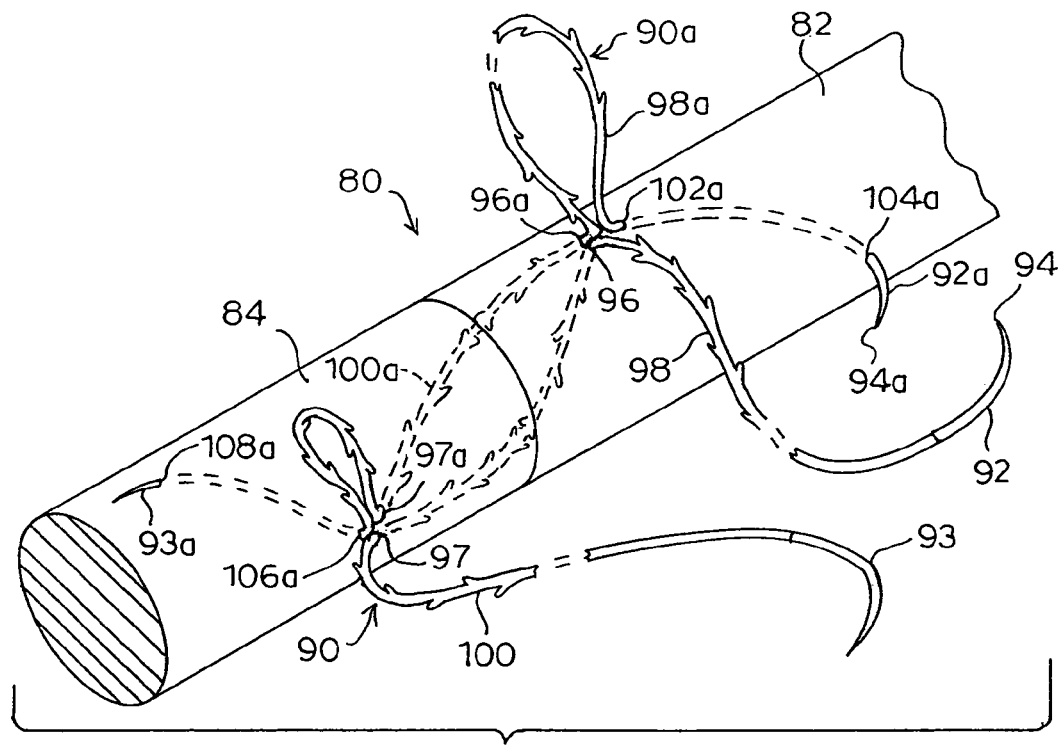
Figure 17:
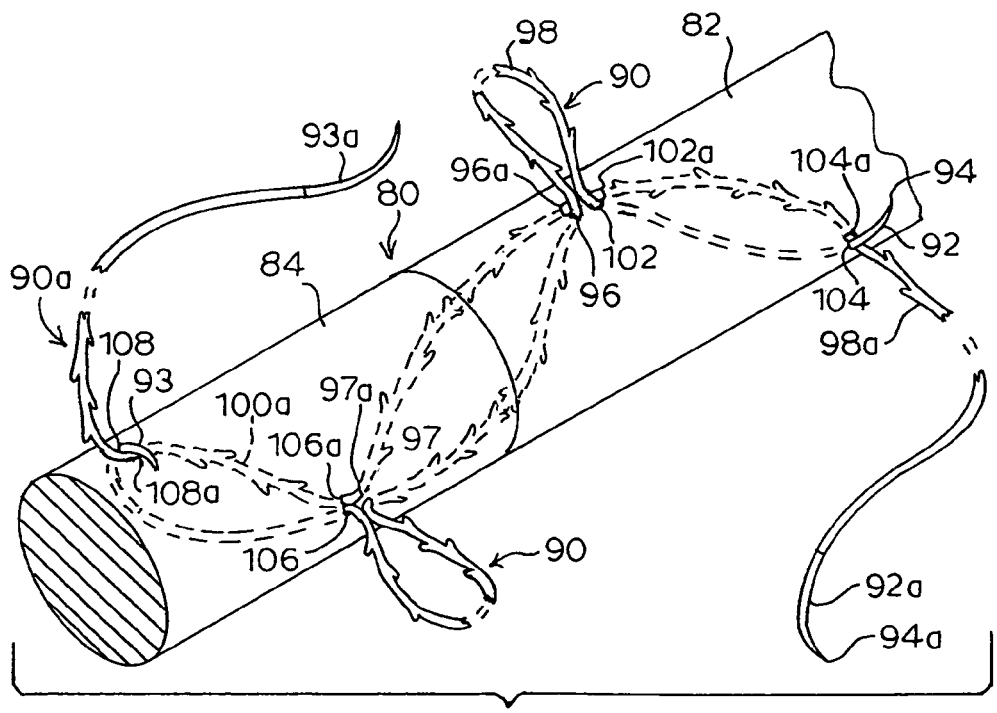

As shown in FIG. 16, the surgeon reinserts the second needle 92a into the periphery of the one end 82 of the tendon 80 at an entry point 102a immediately adjacent the exit point 96a and pushes the needle 92a along a selected curvilinear path until the point 94a of the needle 92a exits the opposite side of the tendon 82 at an exit point 104a that is longitudinally spaced from the entry point 102a. It is understood that the surgeon could use the first exit point 96a as the entry point 102a for the needle 92a if desired. The surgeon pulls the needle 92a out of the tendon 82 for drawing the first portion 98a of the suture 90a through the tendon 82. The surgeon may then reinsert the needle 92a into the tendon 82 at an entry point (not shown) immediately adjacent the exit point 104a and push the needle 92a along a selected curvilinear path and out of the opposite side of the tendon 82 at an exit point (not shown) longitudinally spaced from the previous entry point. It is understood that the surgeon makes as many passes in a "side-to-side" pattern as deemed necessary for holding the end 82 of the tendon 80, or as the length or thickness of the tendon end 82 allows, and removes the remaining length of the first portion 98a of the second suture 90a. With each pass, the longitudinal distance between the entry point and exit point decreases. The surgeon repeats these steps with the second portion 100a of the second suture 90a at the other 84 of the tendon 80. The second end 93a of the suture 90a is inserted into the other end 84 of the tendon 80 at an entry point 106a immediately adjacent the first exit point 97a and advanced along a selected curvilinear path to an exit point 108a opposite and longitudinally spaced from the entry point 106a. The second portion 100a of the second suture 90a is drawn through the tendon 80 leaving a length of the second portion 100a of the suture 90a in the tendon (FIG. 17).

The surgeon repeats the steps described above with the first portion 98 and second portion 100 of the first suture 90 at the ends 82, 84 of the tendon 80. As seen in FIG. 17, the needle 92 at the end of the first portion 98 is inserted into the tendon end 82 at an entry point 102 adjacent the exit point 96 and pushed along a selected curvilinear path until the needle 92 emerges from an exit point 104 in the periphery of the tendon 82 substantially co-located with the second exit point 104a of the first portion 98a of the second suture 90a. In this manner, the surgeon advances longitudinally along the end 82 of the tendon 80 with the first portion 98 of the first suture 90 in a "side-to-side" pattern which generally mirrors that of the first portion 98a of the second suture 90a. Similar steps are taken with the second portion 100 of the first suture 90 in the other end 84 of the tendon 80. The pattern of the first suture 90 and second suture 90a, as well as the respective first portions 98, 98a and second portions 100, 100a of the sutures 90, 90a, generally mirror one another. The exit points and entry points of the sutures are substantially co-located. The ends 82, 84 of the tendon 80 are brought together by pushing the tendon ends along the sutures while maintaining tension on the free ends of the sutures 90, 90a. The barbs 48 maintain the sutures 90, 90a in place and resist movement of the tendon ends 82, 84 away from this position. The needles, along with remaining lengths of the sutures, are cut and discarded. FIGS. 18 and 19 show the suture pattern using the above-described method of the present invention.

It is understood that more sutures may be used in any of the methods of the present invention. The number of sutures used depends on the size, caliber, and length of the tendon to be repaired. Large tendons will require more than two sutures whereas one may suffice for very small tendons. Tendon repair with two sutures according to the present invention exhibits equivalent or better holding power than conventional techniques. Moreover, tendons repaired according to the methods of the present invention maintain their original configuration, profile, contour, and form better when subject to stretching forces. Other methods of tendon repair suitable for use according to the present invention are shown and described in U.S. patent application Ser. No. 09/896,455, entitled "Suture Method", which was filed on Jun. 29, 2001, and which issued on Jul. 29, 2003, as U.S. Pat. No. 6,599,310, the contents of which are hereby incorporated by reference.

Figure 21:
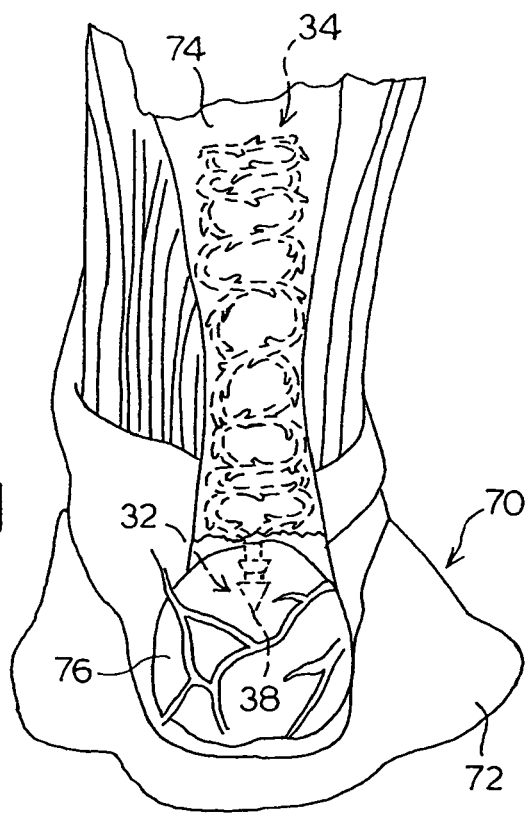
FIGS. 20 and 21 are side and rear elevation views, respectively, of the ankle shown in FIG. 3 with the torn Achilles tendon reattached to the bone using the suture anchor and method shown in FIGS. 7-13 according to the present invention.
Figure 20:
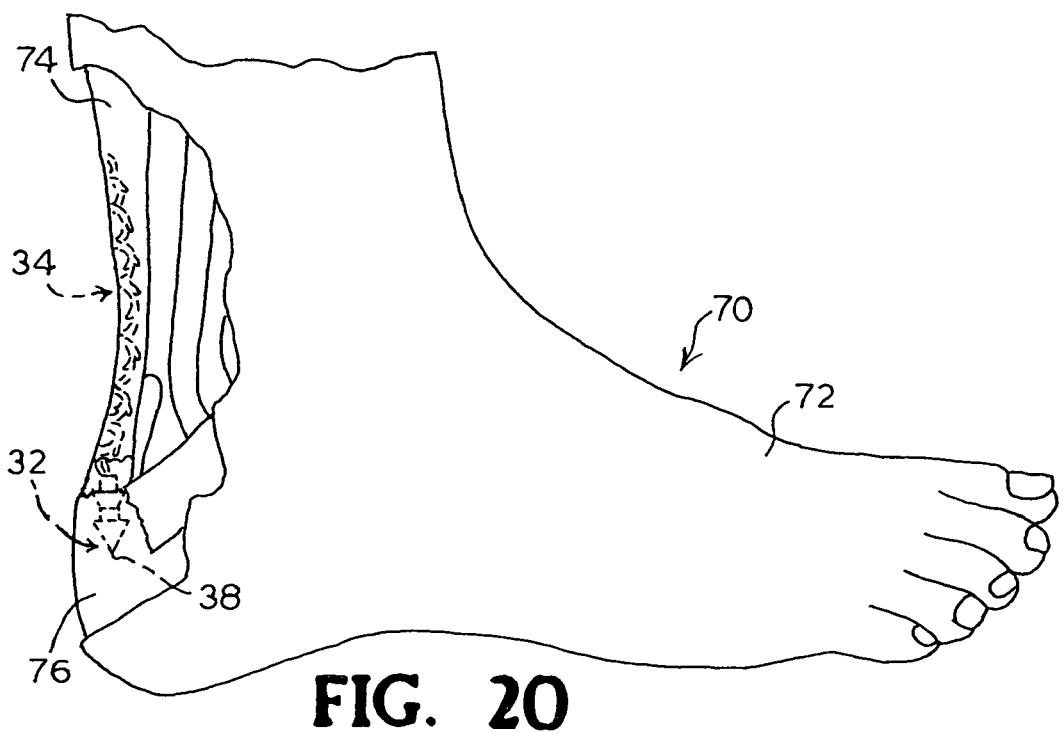

FIGS. 20 and 21 are two views of the Achilles tendon 74 reattached to the heel bone 76 to promote healing according to the present invention using the suture method shown in FIGS. 7-13. The tendon 74 and bone 76 will, over time, grow together.

The present invention provides a compact and easy to use suture anchor and method for reattaching tissue, such as tendons and ligaments, to bone or other connective tissue. The curvilinear placement paths of the suture portion, as contrasted with linear insertion, provide substantially increased biomechanical strength for approximating tissue and bone, or the ends of tendon. The barbed suture portion permits tissue to be approximated and held snug during suturing with less slippage of the suture in the wound. The barbs spread out the holding forces evenly thereby significantly reducing tissue distortion. The suture anchor is useful in endoscopic and arthroscopic procedures and microsurgery. Since knots do not have to be tied, arthroscopic knot tying instruments are unnecessary. If there is an accidental breakage of the barbed suture, the wound is minimally disturbed whereas, with conventional sutures, dehiscence would occur.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. For example, the methods of the present invention can be used with a suture anchor alone as a two-way barbed suture. Accordingly, we intend to cover all such modifications, omissions, additions and equivalents as may be included within the spirit and scope of the invention as defined by the following claims.

We claim:

1. A method for joining one end and another end of a tendon, the method comprising the steps of:
   (a) inserting a first pointed end of a first two-way suture into the one end of the tendon, where the first two-way suture has first and second sharp pointed distal ends for penetrating tissue, a body, a first plurality of barbs extending from the periphery of the body for a first portion of the first suture, the first barbs permitting movement of the first suture through the tissue in a direction of movement of the first end and preventing movement of the first suture relative to the tissue in a direction opposite the direction of movement of the first end, and a second plurality of barbs extending from the periphery of the body for a second portion of the first suture, the second barbs permitting movement of the first suture through the tissue in a direction of movement of the second end and preventing movement of the first suture relative to the tissue in a direction opposite the direction of movement of the second end;
   (b) pushing the first pointed end of the first suture through the tendon along a curvilinear path until the first pointed end of the first suture extends out of the tendon at a first exit point longitudinally spaced from the one end of the tendon;
   (c) gripping the first pointed end of the first suture and pulling the first pointed end out of the tendon for drawing the first portion of the first suture through the tendon and leaving a length of the first portion of the first suture in the tendon between the one end and the exit point;
   (d) inserting the second pointed end of the first suture into the other end of the tendon;
   (e) pushing the second pointed end of the first suture through the tendon along a curvilinear path until the second pointed end of the first suture extends out of the tendon at a second exit point longitudinally spaced from the other end of the tendon;
   (f) gripping the second pointed end of the first suture and pulling the second pointed end out of the tendon for drawing the second portion of the first suture through the tendon and leaving a length of the second portion of the first suture in the tendon between the other end and the second exit point;
   (g) repeating steps (a) through (f) with the first and the second pointed ends of a second two-way suture so that the first and the second exit points of the second suture in the tendon are substantially co-located with the corresponding first and the corresponding second exit points of the first suture and the path of the second suture substantially mirrors the path of the first suture, where the second two-way suture has first and second sharp pointed distal ends for penetrating tissue, a body, a first plurality of barbs extending from the periphery of the body for a first portion of the second suture, the first barbs permitting movement of the second suture through the tissue in a direction of movement of the first end and preventing movement of the second suture relative to the tissue in a direction opposite the direction of movement of the first end, and a second plurality of barbs extending from the periphery of the body for a second portion of the second suture, the second barbs permitting movement of the second suture through the tissue in a direction of movement of the second end and preventing movement of the second suture relative to the tissue in a direction opposite the direction of movement of the second end;
   (h) for a first pass with the first portion of the first suture, reinserting the first pointed end of the first suture into the one end of the tendon at a first entry point immediately adjacent the first exit point of the first suture;
   (i) pushing the first pointed end of the first suture though the tendon along a curvilinear path until the first pointed end of the first suture re-exits out of the same side of the tendon at a re-exit point longitudinally spaced from the first entry point;
   (j) gripping the first pointed end of the first suture and pulling the first pointed end out of the tendon for drawing the first portion of the first suture though the tendon and leaving a length of the first portion of the first suture in the tendon between the first entry point and the re-exit point;
   (k) making as many passes as deemed necessary in a wave-like pattern with the first portion of the first suture;
   (l) repeating steps (h) though (k) with the first portion of the second suture;
   (m) repeating steps (h) though (l) with the respective second portions of the first suture and the second suture;
   (n) bringing the one end and the other end of the tendon together by pushing the tendon ends along the sutures while maintaining tension on the remaining free portions of the sutures; and
   (o) removing the remaining free portions of the sutures.

2. The method as recited in claim 1, wherein one or both of the first and second sharp pointed distal ends of the first suture, one or both of the first and second sharp pointed distal ends of the second suture, or a combination thereof are straight, curved, or a combination thereof.

3. The method as recited in claim 2, wherein one or both of the first and second sharp pointed distal ends of the first suture, one or both of the first and second sharp pointed distal ends of the second suture, or a combination thereof are surgical needles.

4. The method as recited in claim 1, wherein the steps with the first portion of the second suture comprise crossing over the first portion of the first suture.

5. The method as recited in claim 1, wherein the steps with the second portion of the second suture comprise crossing over the second portion of the first suture.

6. The method as recited in claim 1, wherein for each section of the path of the second suture and each respective section of the path of the first suture that mirror each other in tissue:
   said each section of the second suture and said each respective section of the first suture are spaced away from each other in the tissue, and
   the entry and exit points of said each section of the second suture are substantially co-located with the respective entry and exits points of said each respective section of the first suture.

7. The method as recited in claim 1, wherein the tendon is the Achilles tendon.

8. A method for joining one end and another end of a tendon, the method comprising the steps of:
   (a) inserting a first pointed end of a first two-way suture into the one end of the tendon, where the first two-way suture has first and second sharp pointed distal ends for penetrating tissue, a body, a first plurality of barbs extending from the periphery of the body for a first portion of the first suture, the first barbs permitting movement of the first suture through the tissue in a direction of movement of the first end and preventing movement of the first suture relative to the tissue in a direction opposite the direction of movement of the first end, and a second plurality of barbs extending from the periphery of the body for a second portion of the first suture, the second barbs permitting movement of the first suture through the tissue in a direction of movement of the second end and preventing movement of the first suture relative to the tissue in a direction opposite the direction of movement of the second end;
   (b) pushing the first pointed end of the first suture through the tendon along a curvilinear path until the first pointed end of the first suture extends out of the tendon at a first exit point longitudinally spaced from the one end of the tendon;
   (c) gripping the first pointed end of the first suture and pulling the first pointed end out of the tendon for drawing the first portion of the first suture through the tendon and leaving a length of the first portion of the first suture in the tendon between the one end and the exit point;
   (d) inserting the second pointed end of the first suture into the other end of the tendon;
   (e) pushing the second pointed end of the first suture through the tendon along a curvilinear path until the second pointed end of the first suture extends out of the tendon at a second exit point longitudinally spaced from the other end of the tendon;
   (f) gripping the second pointed end of the first suture and pulling the second pointed end out of the tendon for drawing the second portion of the first suture through the tendon and leaving a length of the second portion of the first suture in the tendon between the other end and the second exit point;
   (g) repeating steps (a) through (f) with the first and the second pointed ends of a second two-way suture so that the first and the second exit points of the second suture in the tendon are substantially co-located with the corresponding first and the corresponding second exit points of the first suture and the path of the second suture substantially mirrors the path of the first suture, where the second two-way suture has first and second sharp pointed distal ends for penetrating tissue, a body, a first plurality of barbs extending from the periphery of the body for a first portion of the second suture, the first barbs permitting movement of the second suture through the tissue in a direction of movement of the first end and preventing movement of the second suture relative to the tissue in a direction opposite the direction of movement of the first end, and a second plurality of barbs extending from the periphery of the body for a second portion of the second suture, the second barbs permitting movement of the second suture through the tissue in a direction of movement of the second end and preventing movement of the second suture relative to the tissue in a direction opposite the direction of movement of the second end;
   (h) for a first pass with the first portion of the second suture, reinserting the first pointed end of the second suture into the one end of the tendon at a first entry point immediately adjacent the first exit point of the second suture;
   (i) pushing the first pointed end of the second suture through the tendon along a curvilinear path until the first pointed end of the second suture re-exits out of the same side of the tendon at a re-exit point longitudinally spaced from the first entry point;
   (j) gripping the first pointed end of the second suture and pulling the first pointed end out of the tendon for drawing the first portion of the second suture through the tendon and leaving a length of the first portion of the second suture in the tendon between the first entry point and the re-exit point;
   (k) making as many passes as deemed necessary in a side-to-side pattern with the first portion of the second suture;
   (l) repeating steps (h) through (k) with the second portion of the second suture;
   (m) repeating steps (h) through (l) with the respective first portion and second portion of the first suture;
   (n) bringing the one end and the other end of the tendon together by pushing the tendon ends along the sutures while maintaining tension on the remaining free portions of the sutures; and
   (o) removing the remaining free portions of the sutures.

9. The method as recited in claim 8, wherein one or both of the first and second sharp pointed distal ends of the first suture, one or both of the first and second sharp pointed distal ends of the second suture, or a combination thereof are straight, curved, or a combination thereof.

10. The method as recited in claim 9, wherein one or both of the first and second sharp pointed distal ends of the first suture, one or both of the first and second sharp pointed distal ends of the second suture, or a combination thereof are surgical needles.

11. The method as recited in claim 8, wherein the steps with the passes in a side-to-side pattern with the first portion of the second suture comprise decreasing the longitudinal distance between each respective entry point and exit point of the second suture.

12. The method as recited in claim 8, wherein the steps with the passes in a side-to-side pattern with the second portion of the second suture comprise decreasing the longitudinal distance between each respective entry point and exit point of the second suture.

13. The method as recited in claim 8, wherein for each section of the path of the second suture and each respective section of the path of the first suture that mirror each other in tissue:
  said each section of the second suture and said each respective section of the first suture are spaced away from each other in the tissue, and the entry and exit points of said each section of the second suture are substantially co-located with the respective entry and exits points of said each respective section of the first suture.

14. The method as recited in claim 8, wherein the tendon is the Achilles tendon.

15. A method for repair of tissue in order to attach one end to another end of the tissue, the method comprising the steps of:
  (a) inserting a first pointed end of a first two-way suture into the one end of the tissue, where the first two-way suture has first and second sharp pointed distal ends for penetrating tissue, a body, a first plurality of barbs extending from the periphery of the body for a first portion of the first suture, the first barbs permitting movement of the first suture through the tissue in a direction of movement of the first pointed end and preventing movement of the first suture relative to the tissue in a direction opposite the direction of movement of the first pointed end, and a second plurality of barbs extending from the periphery of the body for a second portion of the first suture, the second barbs permitting movement of the first suture through the tissue in a direction of movement of the second pointed end and preventing movement of the first suture relative to the tissue in a direction opposite the direction of movement of the second pointed end;
  (b) pushing the first pointed end of the first suture through the tissue along a curvilinear path until the first pointed end of the first suture extends out of the tissue at a first exit point longitudinally spaced from the one end of the tissue;
  (c) gripping the first pointed end of the first suture and pulling the first pointed end out of the tissue for drawing the first portion of the first suture through the tissue and leaving a length of the first portion of the first suture in the tissue between the one end and the exit point;
  (d) inserting the second pointed end of the first suture into the other end of the tissue;
  (e) pushing the second pointed end of the first suture through the tissue along a curvilinear path until the second pointed end of the first suture extends out of the tissue at a second exit point longitudinally spaced from the other end of the tissue;
  (f) gripping the second pointed end of the first suture and pulling the second pointed end out of the tissue for drawing the second portion of the first suture through the tissue and leaving a length of the second portion of the first suture in the tissue between the other end and the second exit point;
  (g) repeating steps (a) through (f) with the first and the second pointed ends of a second two-way suture so that the first and the second exit points of the second suture in the tissue are substantially co-located with the corresponding first and the corresponding second exit points of the first suture and the path of the second suture substantially mirrors the path of the first suture, where the second two-way suture has first and second sharp pointed distal ends for penetrating tissue, a body, a first plurality of barbs extending from the periphery of the body for a first portion of the second suture, the first barbs permitting movement of the second suture through the tissue in a direction of movement of the first pointed end and preventing movement of the second suture relative to the tissue in a direction opposite the direction of movement of the first pointed end, and a second plurality of barbs extending from the periphery of the body for a second portion of the second suture, the second barbs permitting movement of the second suture through the tissue in a direction of movement of the second pointed end and preventing movement of the second suture relative to the tissue in a direction opposite the direction of movement of the second pointed end;
  (h) for a first pass with the first portion of the first suture, reinserting the first pointed end of the first suture into the one end of the tissue at a first entry point immediately adjacent the first exit point of the first suture;
  (i) pushing the first pointed end of the first suture through the tissue along a curvilinear path until the first pointed end of the first suture re-exits out of the same side of the tissue at a re-exit point longitudinally spaced from the first entry point;
  (j) gripping the first pointed end of the first suture and pulling the first pointed end out of the tissue for drawing the first portion of the first suture through the tissue and leaving a length of the first portion of the first suture in the tissue between the first entry point and the re-exit point;
  (k) making as many passes as deemed necessary in a wave-like pattern with the first portion of the first suture;
  (l) repeating steps (h) through (k) with the first portion of the second suture;
  (m) repeating steps (h) through (l) with the respective second portions of the first suture and the second suture;
  (n) bringing the one end and the other end of the tissue together by pushing the tissue ends along the sutures while maintaining tension on the remaining free portions of the sutures; and
  (o) removing the remaining free portions of the sutures.

16. The method as recited in claim 15, wherein one or both of the first and second sharp pointed distal ends of the first suture, one or both of the first and second sharp pointed distal ends of the second suture, or a combination thereof are straight, curved, or a combination thereof.

17. The method as recited in claim 16, wherein one or both of the first and second sharp pointed distal ends of the first suture, one or both of the first and second sharp pointed distal ends of the second suture, or a combination thereof are surgical needles.

18. The method as recited in claim 15, wherein the steps with the first portion of the second suture comprise crossing over the first portion of the first suture.

19. The method as recited in claim 15, wherein the steps with the second portion of the second suture comprise crossing over the second portion of the first suture.

20. The method as recited in claim 15, wherein for each section of the path of the second suture and each respective section of the path of the first suture that mirror each other in the tissue:
  said each section of the second suture and said each respective section of the first suture are spaced away from each other in the tissue, and the entry and exit points of said each section of the second suture are substantially co-located with the respective entry and exits points of said each respective section of the first suture.

21. A method for repair of tissue in order to attach one end to another end of the tissue, the method comprising the steps of:
(a) inserting a first pointed end of a first two-way suture into the one end of the tissue, where the first two-way suture has first and second sharp pointed distal ends for penetrating tissue, a body, a first plurality of barbs extending from the periphery of the body for a first portion of the first suture, the first barbs permitting movement of the first suture through the tissue in a direction of movement of the first pointed end and preventing movement of the first suture relative to the tissue in a direction opposite the direction of movement of the first pointed end, and a second plurality of barbs extending from the periphery of the body for a second portion of the first suture, the second barbs permitting movement of the first suture through the tissue in a direction of movement of the second pointed end and preventing movement of the first suture relative to the tissue in a direction opposite the direction of movement of the second pointed end;
(b) pushing the first pointed end of the first suture through the tissue along a curvilinear path until the first pointed end of the first suture extends out of the tissue at a first exit point longitudinally spaced from the one end of the tissue;
(c) gripping the first pointed end of the first suture and pulling the first pointed end out of the tissue for drawing the first portion of the first suture through the tissue and leaving a length of the first portion of the first suture in the tissue between the one end and the exit point;
(d) inserting the second pointed end of the first suture into the other end of the tissue;
(e) pushing the second pointed end of the first suture through the tissue along a curvilinear path until the second pointed end of the first suture extends out of the tissue at a second exit point longitudinally spaced from the other end of the tissue;
(f) gripping the second pointed end of the first suture and pulling the second pointed end out of the tissue for drawing the second portion of the first suture through the tissue and leaving a length of the second portion of the first suture in the tissue between the other end and the second exit point;
(g) repeating steps (a) through (f) with the first and the second pointed ends of a second two-way suture so that the first and the second exit points of the second suture in the internal tissue are substantially co-located with the corresponding first and the corresponding second exit points of the first suture and the path of the second suture substantially mirrors the path of the first suture, where the second two-way suture has first and second sharp pointed distal ends for penetrating tissue, a body, a first plurality of barbs extending from the periphery of the body for a first portion of the second suture, the first barbs permitting movement of the second suture through the tissue in a direction of movement of the first pointed end and preventing movement of the second suture relative to the tissue in a direction opposite the direction of movement of the first pointed end, and a second plurality of barbs extending from the periphery of the body for a second portion of the second suture, the second barbs permitting movement of the second suture though the tissue in a direction of movement of the second pointed end and preventing movement of the second suture relative to the tissue in a direction opposite the direction of movement of the second pointed end;
(h) for a first pass with the first portion of the second suture, reinserting the first pointed end of the second suture into the one end of the tissue at a first entry point immediately adjacent the first exit point of the second suture;
(i) pushing the first pointed end of the second suture though the tissue along a curvilinear path until the first pointed end of the second suture re-exits out of the same side of the tissue at a re-exit point longitudinally spaced from the first entry point;
(j) gripping the first pointed end of the second suture and pulling the first pointed end out of the tissue for drawing the first portion of the second suture though the tissue and leaving a length of the first portion of the second suture in the tissue between the first entry point and the re-exit point;
(k) making as many passes as deemed necessary in a side-to-side pattern with the first portion of the second suture;
(l) repeating steps (h) though (k) with the second portion of the second suture;
(m) repeating steps (h) through (l) with the respective first portion and second portion of the first suture;
(n) bringing the one end and the other end of the tissue together by pushing the tissue ends along the sutures while maintaining tension on the remaining free portions of the sutures; and
(o) removing the remaining free portions of the sutures.

22. The method as recited in claim 21, wherein one or both of the first and second sharp pointed distal ends of the first suture, one or both of the first and second sharp pointed distal ends of the second suture, or a combination thereof are straight, curved, or a combination thereof.

23. The method as recited in claim 22, wherein one or both of the first and second sharp pointed distal ends of the first suture, one or both of the first and second sharp pointed distal ends of the second suture, or a combination thereof are surgical needles.

24. The method as recited in claim 21, wherein the steps with the passes in a side-to-side pattern with the first portion of the second suture comprise decreasing the longitudinal distance between each respective entry point and exit point of the second suture.

25. The method as recited in claim 21, wherein the steps with the passes in a side-to-side pattern with the second portion of the second suture comprise decreasing the longitudinal distance between each respective entry point and exit point of the second suture.

* * * * *